US010702320B2

(12) United States Patent
Archbold

(10) Patent No.: US 10,702,320 B2
(45) Date of Patent: Jul. 7, 2020

(54) MAGNETIC CORE BONE SCREW

(71) Applicant: Christopher A. Archbold, Mission Viejo, CA (US)

(72) Inventor: Christopher A. Archbold, Mission Viejo, CA (US)

( * ) Notice: Subject to any disclaimer, the term of this patent is extended or adjusted under 35 U.S.C. 154(b) by 198 days.

(21) Appl. No.: 15/862,017

(22) Filed: Jan. 4, 2018

(65) Prior Publication Data

US 2019/0021776 A1 Jan. 24, 2019

Related U.S. Application Data

(60) Provisional application No. 62/535,706, filed on Jul. 21, 2017.

(51) Int. Cl.
*A61B 17/86* (2006.01)
*A61B 17/00* (2006.01)
*A61B 17/56* (2006.01)

(52) U.S. Cl.
CPC ........ *A61B 17/8605* (2013.01); *A61B 17/861* (2013.01); *A61B 17/864* (2013.01); *A61B 17/8625* (2013.01); *A61B 17/8635* (2013.01); *A61B 2017/00876* (2013.01); *A61B 2017/567* (2013.01)

(58) Field of Classification Search
CPC ... A61B 17/86; A61B 17/861; A61B 17/8635; A61B 17/8625
See application file for complete search history.

(56) References Cited

U.S. PATENT DOCUMENTS

| | | | |
|---|---|---|---|
| 6,387,096 B1 | 5/2002 | Hyde, Jr. | |
| 8,029,570 B2 | 10/2011 | Barnes et al. | |
| 8,568,457 B2 | 10/2013 | Hunziker | |
| 8,579,947 B2 | 11/2013 | Wu | |
| 2003/0236572 A1* | 12/2003 | Bertram, III | A61F 2/32 623/18.12 |
| 2004/0059423 A1* | 3/2004 | Barnes | A61B 17/58 623/18.12 |
| 2006/0074448 A1 | 4/2006 | Harrison | |
| 2008/0255556 A1* | 10/2008 | Berger | A61B 17/8605 606/60 |
| 2009/0099404 A1* | 4/2009 | Kraus | A61B 17/86 600/13 |
| 2014/0025122 A1 | 1/2014 | Cook et al. | |
| 2016/0242820 A1* | 8/2016 | Whipple | A61B 17/7055 |

* cited by examiner

*Primary Examiner* — Christopher J Beccia
(74) *Attorney, Agent, or Firm* — Cionca IP Law P.C.; Marin Cionca

(57) ABSTRACT

A bone screw configured to be screwed into a bone having: an exterior casing; a head having a head interior surface; a tip configured to be driven into the bone; a shaft extending between the head and the tip, the shaft having exterior threads; a magnet; an interior cavity within the bone screw configured to house the magnet; a cap having: a top end having a recess configured to receive a means for driving the bone screw into the bone; and a bottom end having cap threads; the head being configured to receive the cap by having interior threads on the head interior surface; wherein an association of the cap threads with the interior threads causes the cap to be sealed to the head, and thus causes the magnet to be encased within the bone screw with no portion of the magnet exposed outside of the exterior casing.

20 Claims, 8 Drawing Sheets

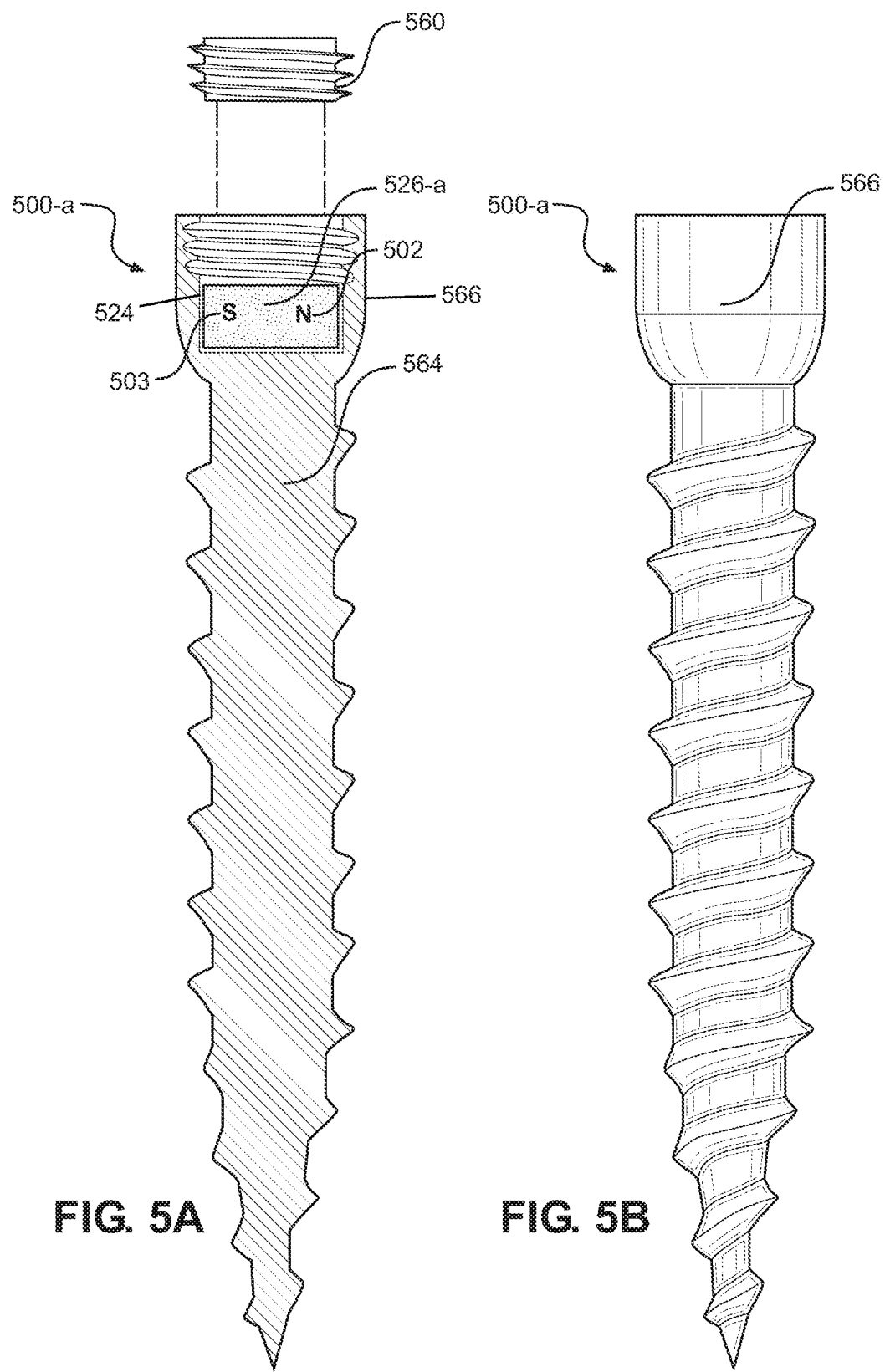

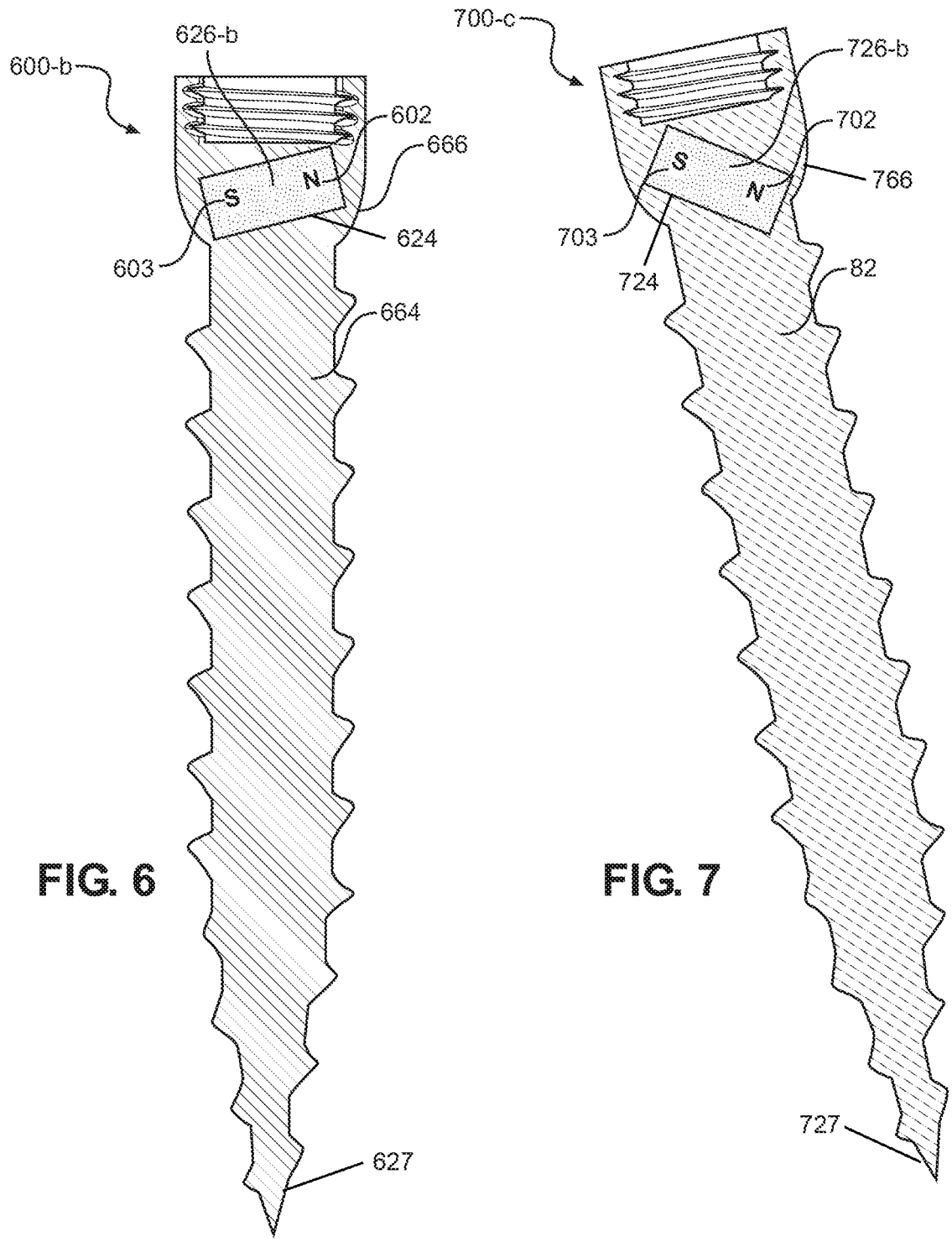

MAGNETIC CORE BONE SCREW

CROSS-REFERENCE TO RELATED APPLICATIONS

This application claims the benefit of U.S. Provisional Application No. 62/535,706, filed Jul. 21, 2017, which is hereby incorporated by reference, to the extent that it is not conflicting with the present application.

BACKGROUND OF INVENTION

1. Field of the Invention

The invention relates generally to surgical and orthopedic devices and more specifically to bone screws.

2. Description of the Related Art

Magnets implanted in bones during surgery on the bones may be used for correcting problems in patients' bones. These problems may include bones pressing on nerves in the spinal column, for example, but procedures to implant magnets may often require additional materials such as brackets or other similar apparatuses to hold the magnets in place, or may require several steps to implant the magnets inside the bones. These types of procedures may be invasive and may also introduce the risk of rejection of the implanted materials by the body. Ferrous magnetic screws including strong neodymium magnetic screws used for such procedures may be subject to rejection when implanted in the body. Coatings placed on the magnets to prevent such rejection may also wear off over time. Such procedures can thus cause potential problems to the patient, or may not be options for certain patients. Thus, there is a need for a solution to these problems.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a bone screw configured to be screwed into a bone is provided, comprising: an exterior casing; a head having a head interior surface; a tip having a point configured to be driven into the bone; a shaft extending between the head and the tip; a magnet having a north pole and a south pole; an interior cavity within the bone screw configured to house the magnet; a cap having: a top end having a recess configured to receive a means for driving the bone screw into the bone; and a bottom end having a set of cap threads; wherein the exterior casing encloses the tip, the shaft, at least a portion of the cap, and at least a portion of the head, and wherein a portion of the exterior casing enclosing the shaft comprises a set of exterior threads; the head being configured to receive the cap by having a set of interior threads on the head interior surface; and wherein an association of the set of cap threads with the set of interior threads causes the cap to be sealed to the head, and thus causes the magnet to be encased within the bone screw with no portion of the magnet exposed outside of the exterior casing. An advantage may be that a plurality of magnetic core bone screws may be used for aligning bones of the body into a correct physiologic position using a minimally invasive surgical technique, without the need for brackets or additional apparatuses to connect the screws to the bones, and without the need for additional steps in the surgery to apply such brackets. Another advantage may be that the complete encasing of the magnet within the screw may reduce the potential for rejection by the body, such that implantation of strongly magnetic material into the bone using a minimally invasive technique may be achieved while reducing risk of rejection of the implanted materials in the patient. Another advantage may be that orthopedic movement of the bones may be achieved with a minimally invasive surgical technique with fewer steps than is required by techniques known in the art.

In another aspect, a bone screw configured to be screwed into a bone is provided, comprising: an exterior casing; a head having a recess on a top end, the recess being configured to receive a means for driving the bone screw into the bone; a tip having a point configured to be driven into the bone; a shaft extending between the head and the tip; a magnet having a north pole and a south pole; an interior cavity within the bone screw configured to house the magnet, the interior cavity being located inside of the shaft, such that a length of the magnet extending between the north pole and the south pole is parallel to the shaft; wherein the exterior casing encloses the tip, the shaft, and the head, and wherein a portion of the exterior casing enclosing the shaft comprises a set of exterior threads; and wherein the magnet is encased within the bone screw with no portion of the magnet exposed outside of the exterior casing. Again, an advantage may be that a plurality of magnetic core bone screws may be used for aligning bones of the body into a correct physiologic position using a minimally invasive surgical technique, without the need for brackets or additional apparatuses to connect the screws to the bones, and without the need for additional steps in the surgery to apply such brackets. Another advantage may be that the complete encasing of the magnet within the screw may reduce the potential for rejection by the body, such that implantation of strongly magnetic material into the bone using a minimally invasive technique may be achieved while reducing risk of rejection of the implanted materials in the patient. Another advantage may be that orthopedic movement of the bones may be achieved with a minimally invasive surgical technique with fewer steps than is required by techniques known in the art.

In another aspect, a bone screw configured to be screwed into a bone, comprising: an exterior casing; a head having a recess on a top end, the recess being configured to receive a means for driving the bone screw into the bone; a tip having a point configured to be driven into the bone; a shaft extending between the head and the tip; a magnet having a north pole and a south pole; an interior cavity within the bone screw configured to house the magnet, the interior cavity being located inside of the head; wherein the exterior casing encloses the tip, the shaft, and the head, and wherein a portion of the exterior casing enclosing the shaft comprises a set of exterior threads; and wherein the magnet is encased within the bone screw with no portion of the magnet exposed outside of the exterior casing. An advantage may be that the head of the screw may be used for aligning with other magnetic core bone screws, to achieve the selected positioning of the bones. Again, an advantage may be that a plurality of magnetic core bone screws may be used for aligning bones of the body into a correct physiologic position using a minimally invasive surgical technique, without the need for brackets or additional apparatuses to connect the screws to the bones, and without the need for additional steps in the surgery to apply such brackets. Another advantage may be that the complete encasing of the magnet within the screw may reduce the potential for rejection by the body, such that implantation of strongly magnetic material into the bone using a minimally invasive technique may be achieved while reducing risk of rejection of the implanted materials in the patient. Another advantage may be that orthopedic movement of the bones may be achieved with a minimally invasive surgical technique with fewer steps than is required by techniques known in the art.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which:

FIGS. 5A-5B illustrate a side sectional view and a side view, respectively, of another example of a magnetic core bone screw having a magnetic core located inside the head of the screw, according to an aspect.

FIG. 6 illustrates a side sectional view another example of the magnetic core bone screw, having a magnet placed at an angle inside the screw head, according to an aspect.

FIG. 7 illustrates a side sectional view of another example of the magnetic core bone screw having a magnet placed at an angle inside the screw head, according to an aspect.

DETAILED DESCRIPTION

Figures 1A, 1B:
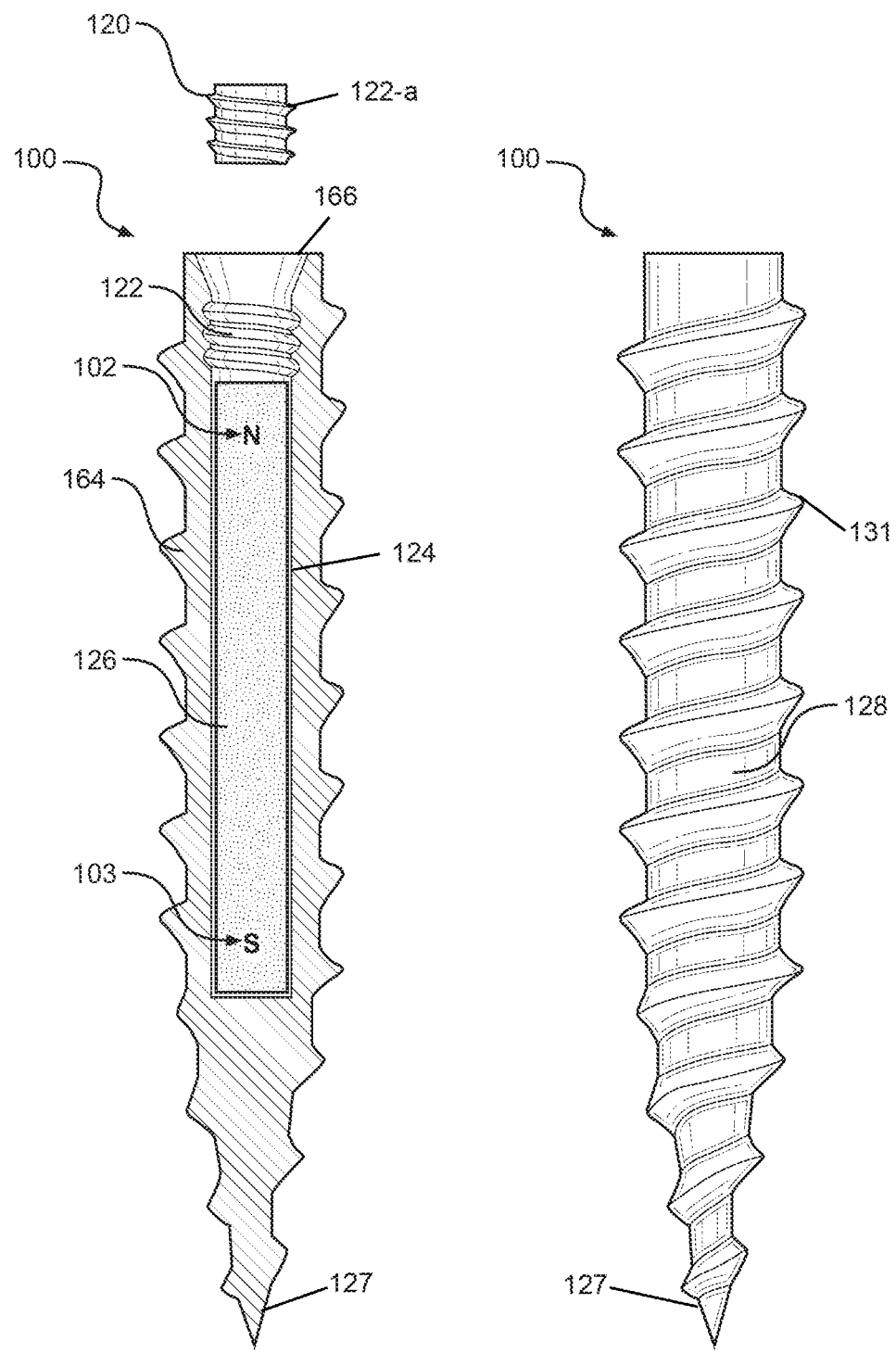
FIGS. 1A-1B illustrate a side sectional view and a side view, respectively, of a magnetic core bone screw, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures (e.g., 103 and 403, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

FIGS. 1A-1B illustrate a side sectional view and a side view, respectively, of a magnetic core bone screw ("magnetic core bone screw," or "bone screw") 100, according to an aspect. Bone screws 100 containing magnetic cores may screwed into the vertebrae or other bones of the body with a screwdriver, for example, or any other suitable means. The bone screw 100 may include a head 166, which may be associated with a screw cap 120, a shaft 164, and a tip 127 at the opposite end of the head 166 which may be pointed to aid in the drilling and the insertion of the bone screw 100 into a bone. The shaft 164 may extend between the head 166 and the tip 127. The bone screw may be provided with an inner cavity or chamber 124 for housing a magnet 126, which may thus become the magnetic core 126 ("magnetic core," or "magnet") of the bone screw. The magnet 126 may, for example, be neodymium, or any other suitable material. As an example, the magnetic core 126 may be housed within a chamber 124 located in the shaft 164 of the bone screw 100. The magnet 126 having a north pole 102 and a south pole 103 may be placed in the interior cavity 124 of the bone screw 100 as shown in FIG. 1A such that the magnet is not visible from the exterior of the screw, as shown by FIG. 1B. The exterior casing 128 of the screw 100, which may completely surround and encase the magnet 126, may be constructed from a material not likely or less likely to be rejected by the human body, such as, for example, titanium or ceramic materials. An advantage may be that additional coatings may not be needed on the magnet itself, thus again reducing the risk of rejection of materials by the patient's body. A complete encasing of the magnet 126 by the exterior casing 128 may thus reduce the risk to a patient of injury, rejection of implanted materials, or complications following a surgery.

The bone screw 100 may also be provided with interior threads 122 at a top end of the screw at the head 166, and the inner threads 122 may be threaded or associated with the cap threads of 122-*a* of a top screw cap ("top screw cap," "screw cap" or "cap") 120. The cap 120 may then seal in the magnet 126 such that no portion of the magnet is exposed or visible outside of the exterior casing 128 of bone screw 100, and the cap may be constructed from the same or similar material as the exterior casing 128. The cap 120 may allow for the magnet 126 to be removably inserted into the bone screw, and replaced or repositioned as needed, for example. As shown by FIG. 1B, the bone screw 100 may be provided with exterior threads 131 on the exterior casing 128 surface, which may aid a user in screwing, drilling, or inserting the bone screw 100 into bone.

The magnetic core bone screws 100 may be used to help relocate or align bones to the correct anatomical position, to correct problems or to relieve pain or pressure, for example. As examples, the screws may be used to align vertebrae, or to separate vertebrae that are pinching a nerve. For example, for patients or users suffering from an undesired curvature of the spine, the magnetic core bone screws 100 may be placed in several vertebrae in series such that the vertebral column may be brought into a proper or desired alignment. Magnetic core bone screws 100 may be used as a part of a minimally invasive surgical technique. An advantage may be that this method of implanting magnets into bones may require fewer steps to complete the operation than other known methods. As an example, the magnetic core bone screws 100 may be placed into vertebrae, or any other suitable bones of the body. In the spine, orthopedic movement of vertebrae may be achieved by using magnetic core screws inserted into the vertebrae to attract or repel adjacent magnetic core screws screwed into neighboring vertebrae. The magnetic core bone screws may also be used alone or in tandem with other therapies to align the spine for those that suffer from improper curvature such as that which may occur in scoliosis. For example, another therapy or technique that the magnetic core bone screws may be used with is the attachment or placement of external magnets, which may be strapped into fixed positions outside of the body of the patient or the user, which may assist in bringing bones which have magnetic core bone screws drilled into them into a proper or desired position or alignment over time. As another example of an additional therapy or technique that may be used with magnetic core bone screws drilled into a patient's bones, the body or a portion of the body may be placed into an external electromagnetic field which may be used to bring bones containing the magnetic core bone screws into a proper or desired position or alignment. As another example, a patient or user suffering from bones that are too short may have magnetic core bone screws drilled into their bones, and next be placed into an external electromagnetic field in order to lengthen the bone by taking advantage of the magnetic pull on each end of the drilled bones, over time.

Another advantage may be that this minimally invasive technique may require no brackets or other apparatuses to be attached to the bones or vertebrae, thus requiring less materials and less potential risk of rejection of the inserted materials in the patient. Brackets for holding a magnet to the bones may be eliminated from the process, and multiple steps for inserting a magnet into the bone may be reduced only to the step of screwing the bone screw with an embedded or encased magnet into the bone. Thus, another advantage may be that these surgical procedures may be more efficient than previously known techniques.

The magnetic core bone screws may be constructed to be the size of conventional bone screws as known in the art, or may be constructed to be slender enough to fit through the thickness of a hypodermic needle. Another advantage may be that the magnet embedded within the bone screw may require no additional coating, being encased completely within the bone screw itself.

Figure 2:
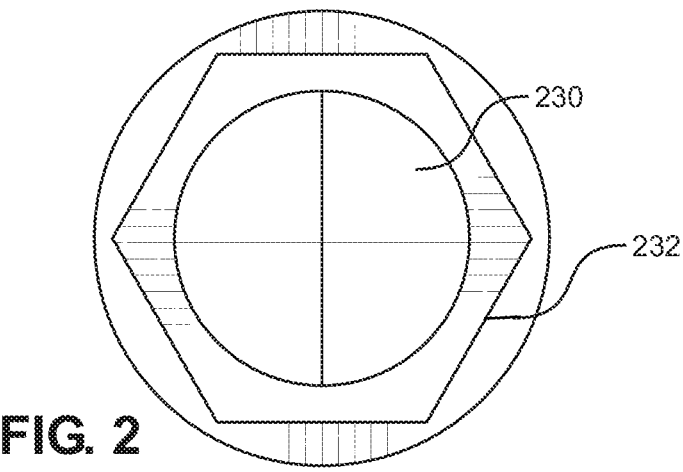
FIG. 2 illustrates the top view of the screw cap on a bone screw, according to an aspect.

FIG. 2 illustrates the top view of the screw cap ("screw cap" or "cap") 220 on a bone screw 200, according to an aspect. As an example, the screw cap 220 may be provided with a recess or screw drive, configured to receive any means or tool for driving the bone screw 200 into a bone. As an example, the bone screw may be provided with a recess or screw drive such as, for example, a Phillips head as shown by 230, or any other suitable type of screw drive. The bone screw 200 may also be constructed with a screw drive such as an Allen's head 232 shown as an example, or any other suitable type of screw drive, which may be used for receiving a means for driving the screw 200 into the bone.

Figure 3:
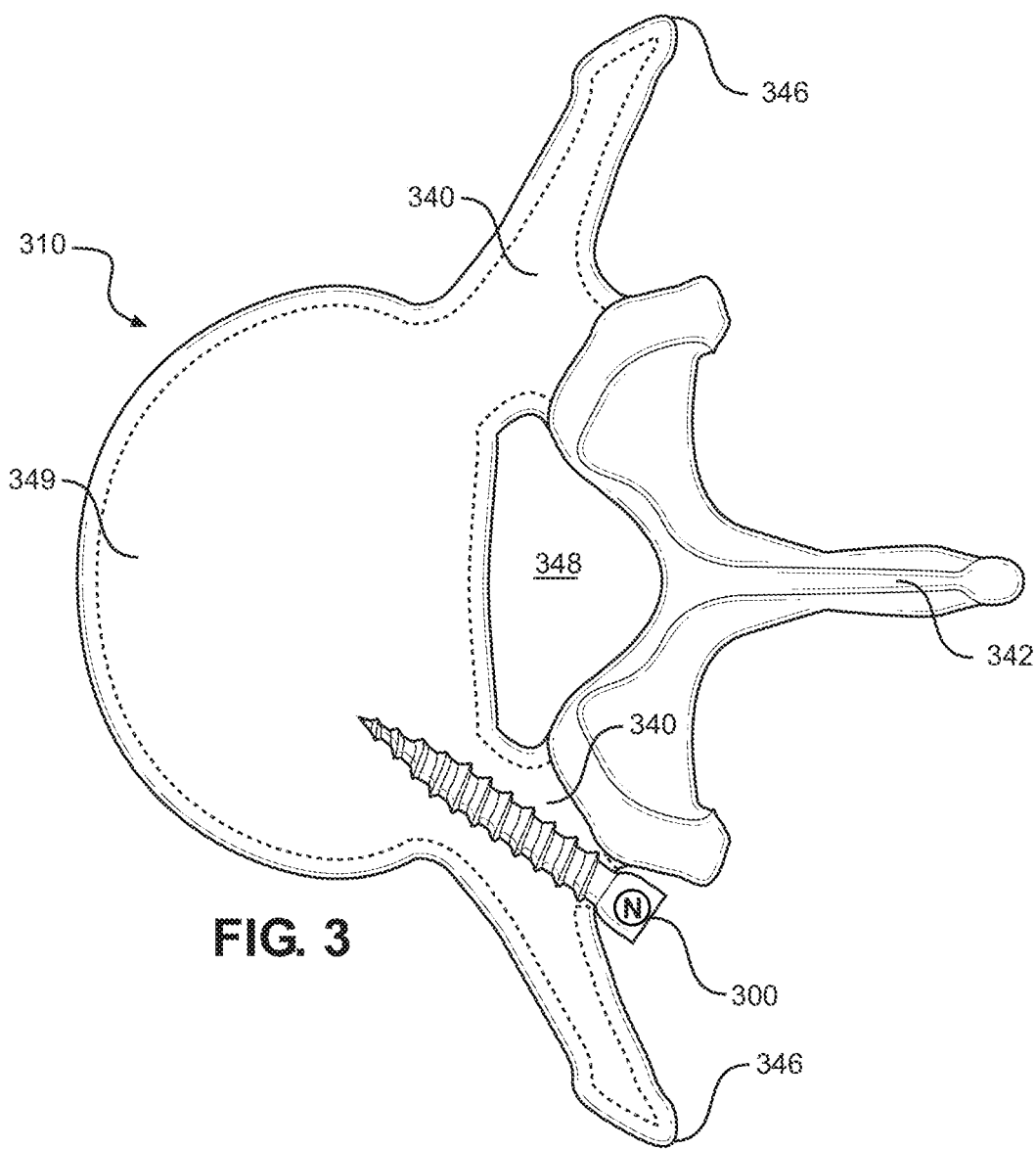
FIG. 3 illustrates the superior (top) view of a vertebra with a magnetic core bone screw 300 screwed into the interior of the vertebral body of the vertebral bone, according to an aspect.

FIG. 3 illustrates the superior (top) view of a vertebra 310 with a magnetic core bone screw 300 screwed into the interior of the vertebral body 349 of the vertebral bone 310, according to an aspect. The spinous process 342, transverse processes 340, the tip of the transverse processes 346, the vertebral foramen 348, and the vertebral body 349 may be visible from the superior view of the vertebra, as shown. The magnet (not visible) within the magnetic core bone screw 300 may be located in the shaft of the magnetic core bone screw (as shown by 126 in FIG. 1A).

The bone screw 300 having a magnet may be screwed into the vertebrae 310 in order to take advantage of or employ the attraction and repulsion characteristics of magnetic fields. These forces may be used to align vertebrae, separate vertebrae or bring vertebrae closer together, according to the medical needs of the user. These forces may be used to bring bones of the body closer together or farther apart. These techniques may be used alone or in combination with other conventional orthopedic techniques for either minor or major bone or vertebral movement, for example. The magnetic core bone screw 300 may be placed anywhere into a bone, such as a vertebra, for example, such that the magnetic forces of the screws may produce the desired result. As an example, for achieving a correct positioning of the vertebrae, a magnetic core bone screw or a plurality of screws may normally be screwed into a vertebra, and an additional screw or plurality of screws may be screwed into an accompanying nearby vertebra, to creates the repulsion or attraction force that move the vertebrae to the desired position. The magnetic core bone screws 300 may be screwed into several vertebrae in series to achieve the desired result for the vertebral column. Magnetic core bone screws may also be screwed into other bones of the body to similarly attain and/or retain the proper physiologic placement of the bones.

Figure 4:
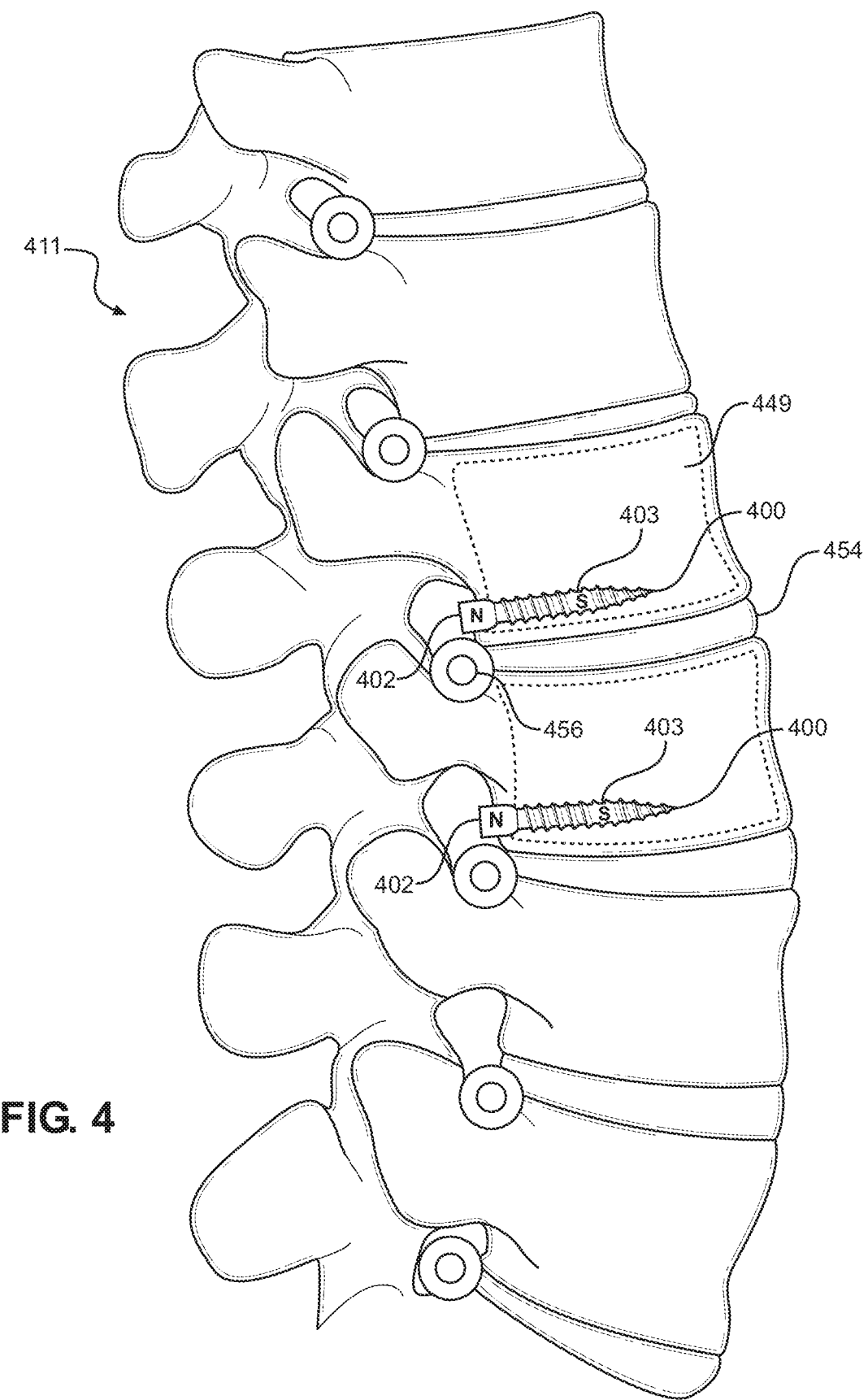
FIG. 4 illustrates the lateral (side) view of the spinal column with inserted magnetic core bone screws, according to an aspect.

FIG. 4 illustrates the lateral (side) view of the spinal column 411 with inserted magnetic core bone screws 400, according to an aspect. The body 449 of the individual vertebra, the intervertebral disc 454, and the spinal nerve 456 are visible in this exemplary view. The repulsion of the magnets inside the magnetic core bone screws 400 may help to relieve pressure on the spinal nerve 456. Again, the magnetic core bone screws 400 may have the magnets located inside the shaft of the screws. An exemplary alignment of the north and south poles of the magnets are shown by 402 and 403, respectively. A plurality of bone screws 400 may be inserted into the vertebrae with their north poles 402 and south poles 403 aligned such that a repulsion is caused between the magnets.

FIGS. 5A-5B illustrate a side sectional view and a side view, respectively, of another example of a magnetic core bone screw 500-*a* having a magnetic core located inside the head 566 of the screw 500-*a*, according to an aspect. The magnet 526-*a* may be positioned perpendicular to the shaft 564 of the screw at a 90-degree angle, as shown, and may have a north pole 502 and south pole 503. The floor of the interior cavity 524 may be perpendicular to the shaft, such that the length of the magnet extending between the north pole and south pole housed within the cavity is perpendicular to the shaft. The bone screw 500-*a* may be provided with a screw-on cap 560, for example, which may be used for sealing in the magnet 526-*a*.

FIG. 6 illustrates a side sectional view another example of the magnetic core bone screw 600-*b*, having a magnet 626-*b* placed at an angle inside the screw head 666, according to an aspect. As an example, a magnetic core bone screw 600-*b* may have a magnet 626-*b* located within the screw head 666 rather than the shaft 664. The cavity 624 for housing the magnet may thus be within the screw head 666, and the interior cavity may have a floor that is sloped such that the cavity is at an angle other than 90 degrees to the shaft 664 of the bone screw 600-*b*. The interior cavity may be at an angle greater than 90 degrees with respect to the shaft 664, for example. Such an orientation of the magnet 626-*b* within the interior cavity 624 may allow the magnetic field of the magnet 626-*b* to be directed at various angles when screwed into the bone, as needed by the user. The angle of the magnet 626-*b* may be such that the north pole 602 is pointed upwards towards the head 666, and the south pole 603 is pointed downwards towards the tip 627, as an example.

FIG. 7 illustrates a side sectional view of another example of the magnetic core bone screw 700-*c* having a magnet 726-*b* placed at an angle inside the screw head 766, according to an aspect. As another example, and similar to the example showed in FIG. 6, the magnet 726-*b* may be placed with its north pole 702 pointing downwards towards the tip 727 and its south pole 703 pointing upwards towards the head 766, by being housed inside of a cavity 724 with a sloped floor.

Figure 8:
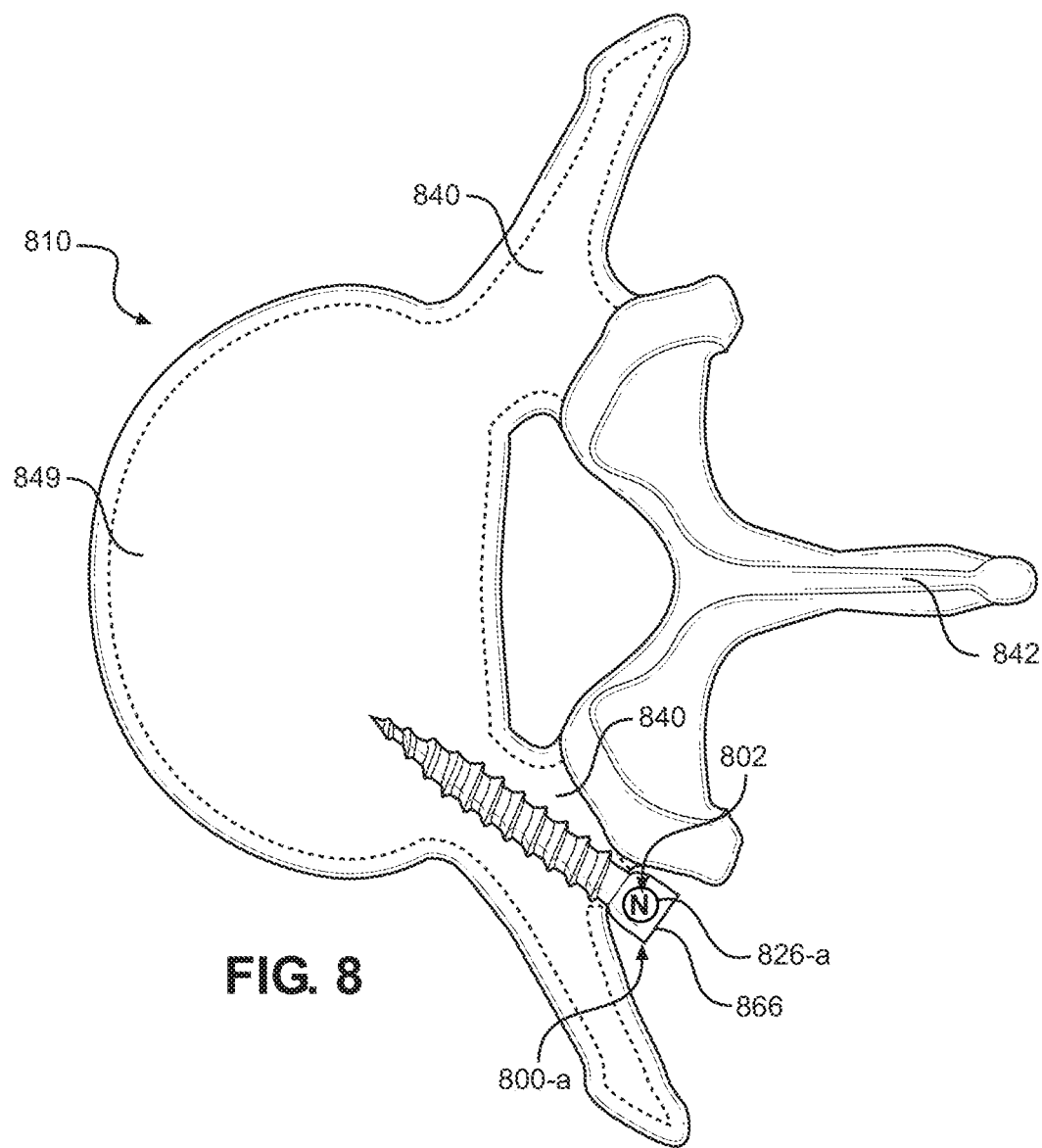
FIG. 8 illustrates the superior (top) view of a vertebra with a magnetic core bone screw 800-*a* screwed into the interior of the vertebral bone body, according to an aspect.

FIG. 8 illustrates the superior (top) view of a vertebra 810 with a magnetic core bone screw 800-*a* screwed into the interior of the vertebral bone body 849, according to an aspect. The transverse processes 840 and the spinous process 842 of the vertebra 810 are visible in this exemplary view. The magnetic core bone screw 800-*a* may have the magnet 826-*a* located in the interior of the head 866 of the screw 800-*a*, and the north pole 802 of the magnet may be pointed towards the superior side of the vertebra 810 with the south pole of the magnet (not visible) may be pointed towards the inferior side of the vertebra, as an example.

Figure 9:
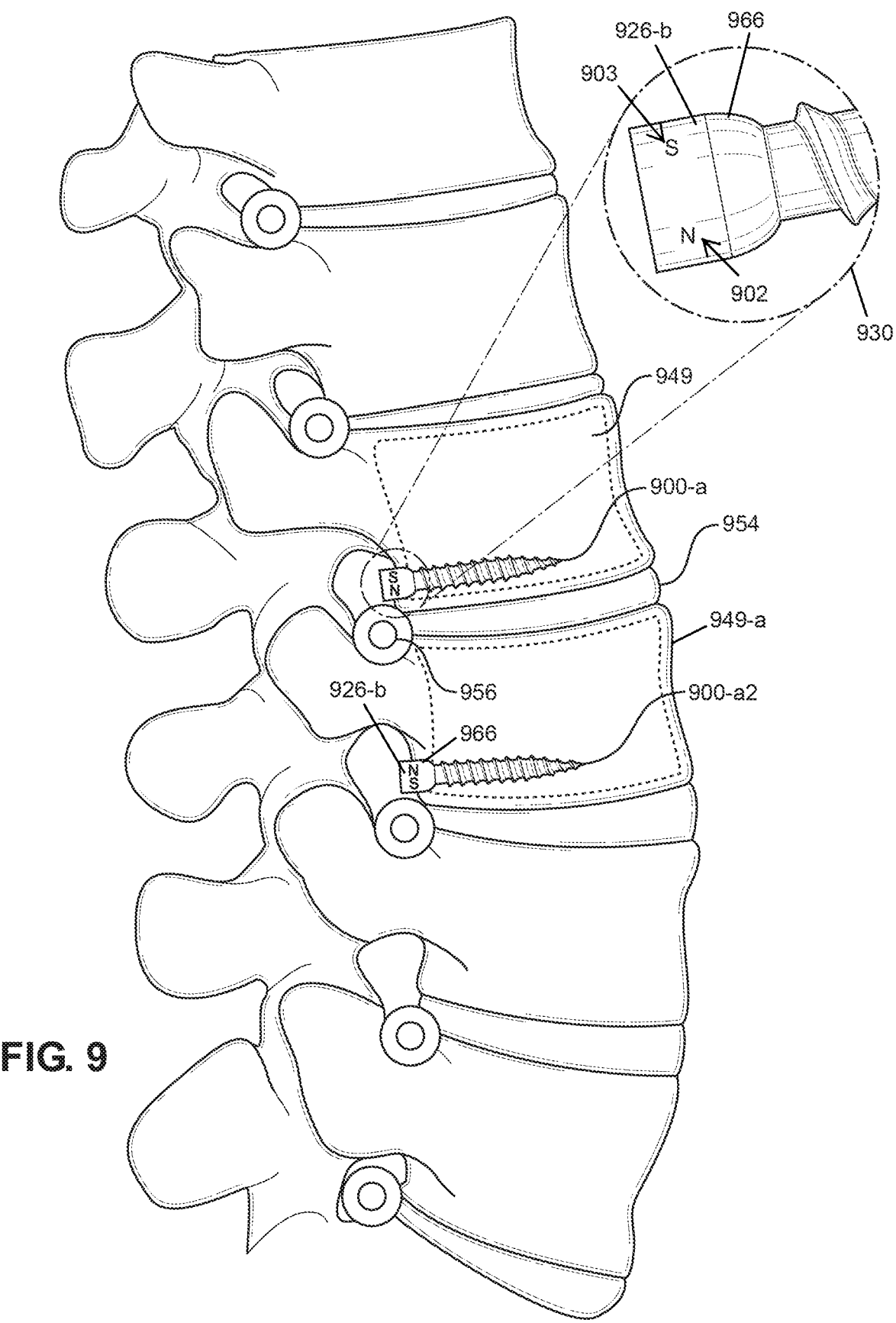
FIG. 9 illustrates another example of the lateral (side) view of the spinal column having magnetic core bone screws inserted, with a detailed enlarged view of a screw head, according to an aspect.

FIG. 9 illustrates another example of the lateral (side) view of the spinal column 911 having magnetic core bone screws 900-*a* inserted, with a detailed enlarged view 930 of a screw head 966, according to an aspect. The body 949 of the individual vertebra, the intervertebral disc 954, and the spinal nerve 956 are visible in this view. Again, similar to the discussion when referring to FIG. 4, the repulsion of the magnets 900-*a* inside the magnetic core bone screws 900-*a* may help to relieve pressure from the vertebrae 949 on the spinal nerve 956. As an example, a first screw 900-*a* having a magnet 926-*b* within the screw head 966 may be positioned in a first vertebra 949 such that the magnet's south pole 903 is pointed upwards towards the superior side of the vertebra, and the magnet's north pole 902 is pointed downwards towards the inferior side of the vertebra, as shown in the detailed enlarged view 930. Next, a second screw 900-*a*2 having a magnet 926-*b* within the screw head 966 may be positioned in a second vertebra 949-*a* on the inferior side of the first vertebra 949. The magnet 926-*b* of the second screw 900-*a*2 may be oriented such that the north pole is facing towards the north pole 902 of the first screw 900-*a*, and the south pole is facing away from the first screw 900-*a*.

Figure 10:
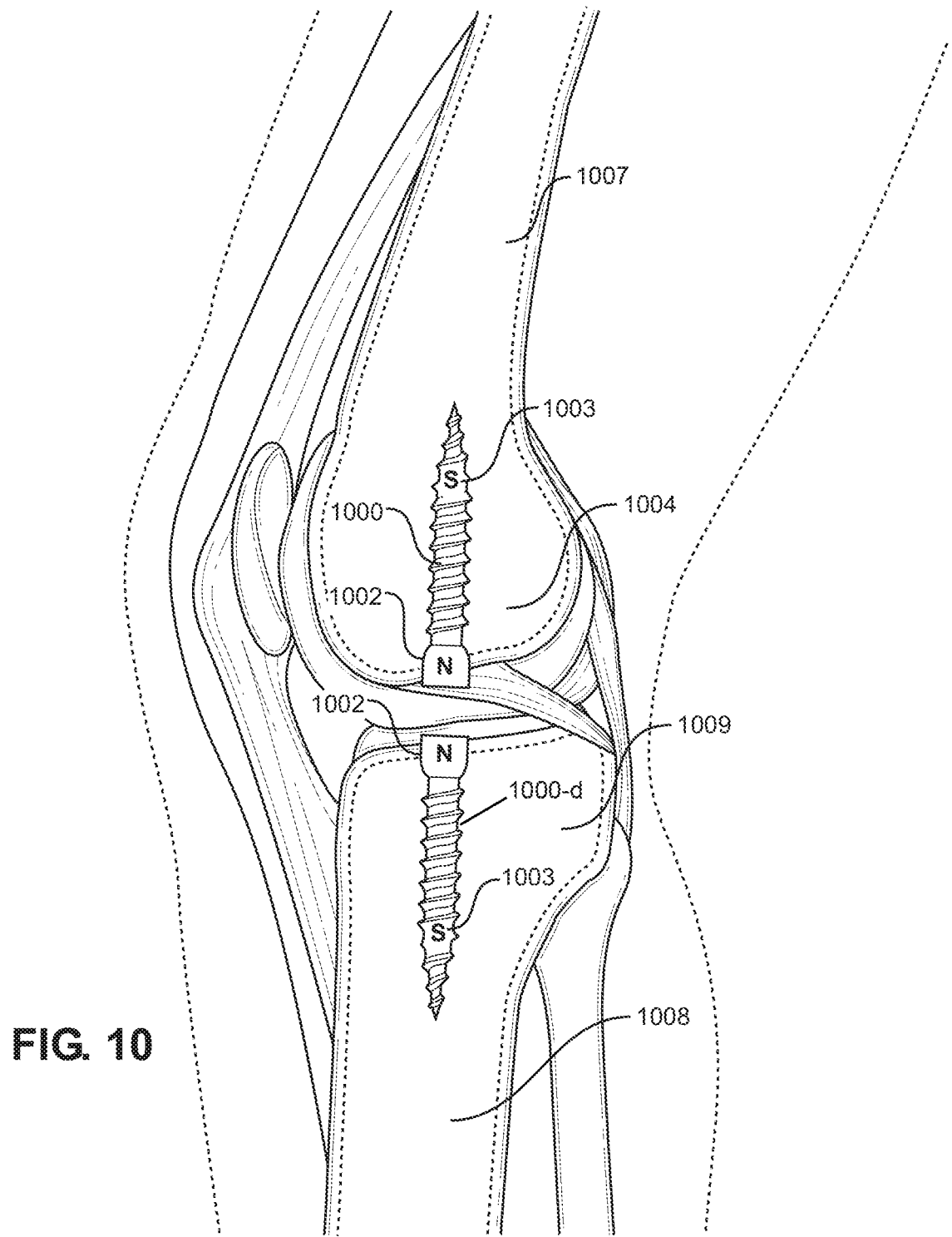
FIG. 10 illustrates the side view of the bones of the leg with inserted magnetic core bone screws, according to an aspect.

FIG. 10 illustrates the side view of the bones of the leg with inserted magnetic core bone screws 1000 and 1000-*d*, according to an aspect. The exemplary view shows an example of magnetic core bone screws 1000 in the tibia 1007 and the femur 1008, with the tibia 1007, medial condyle of the tibia 1004, femur 1008, and the medial epicondyle of the femur 1009 visible. The magnetic core bone screws 1000 may be used in any other suitable bones of the body to acquire the correct anatomical position needed for the patient. As shown as an example, two magnetic core bone screws may be placed across from one another in the tibia and the femur. The north poles 1002 and south poles 1003 of the magnetic core bone screws 1000 may be aligned as shown such that the two bone screws 1000 are repulsed from each other. The exemplary alignment of the first and second magnetic core bone screws may achieve a therapeutic effect or relieve pain or tension in the patient, for example.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A bone screw configured to be screwed into a bone, comprising:
    an exterior casing;
    a head having a head interior surface;
    a tip having a distalmost point configured to be driven into the bone;
    a shaft extending between the head and the tip;
    a magnet having a north pole and a south pole;
    an interior cavity within the bone screw configured to house the magnet;
    a cap having:
        a top end having a recess configured to receive a means for driving the bone screw into the bone; and
        a bottom end having a set of cap threads;
    wherein the exterior casing encloses the tip, the shaft, at least a portion of the cap, and at least a portion of the head, and wherein a portion of the exterior casing enclosing the shaft comprises a set of exterior threads;
    the head being configured to receive the cap by having a set of interior threads on the head interior surface; and
    wherein an association of the set of cap threads with the set of interior threads causes the cap to be sealed to the head, and thus causes the magnet to be encased within the bone screw with no portion of the magnet exposed outside of the exterior casing.

2. The bone screw of claim 1, wherein the interior cavity is within the head.

3. The bone screw of claim 2, wherein a floor of the interior cavity is oriented at an angle greater than 90 degrees with respect to the shaft.

4. The bone screw of claim 2, wherein a floor of the interior cavity is oriented such that a length of the magnet extending between the north pole and the south pole is perpendicular to the shaft.

5. The bone screw of claim 1, wherein the interior cavity is within the shaft, such that a length of the magnet extending between the north pole and the south pole is parallel to the shaft.

6. The bone screw of claim 5, wherein the north pole is oriented towards the head and the south pole is oriented towards the tip.

7. The bone screw of claim 1, wherein the exterior casing is constructed from titanium.

8. The bone screw of claim 1, wherein the exterior casing is constructed from ceramic.

9. The bone screw of claim 1, wherein the magnet is constructed from neodymium.

10. The bone screw of claim 1, wherein the bone is a vertebra.

11. The bone screw of claim 1, wherein the bone screw is configured to be drilled into the bone of a user and aligned with a magnetic field external to the user.

12. A bone screw configured to be screwed into a bone, comprising:
    an exterior casing;
    a head having a recess on a top end, the recess being configured to receive a means for driving the bone screw into the bone;
    a tip having a distalmost point configured to be driven into the bone;
    a shaft extending between the head and the tip;
    a magnet having a north pole and a south pole;
    an interior cavity within the bone screw configured to house the magnet, the interior cavity being located inside of the shaft, such that a length of the magnet extending between the north pole and the south pole is parallel to the shaft;
    wherein the exterior casing encloses the tip, the shaft, and the head, and wherein a portion of the exterior casing enclosing the shaft comprises a set of exterior threads; and
    wherein the magnet is encased within the bone screw with no portion of the magnet exposed outside of the exterior casing.

13. The bone screw of claim 12, wherein the north pole is oriented towards the head and the south pole is oriented towards the tip.

14. The bone screw of claim 12, wherein the exterior casing is constructed from titanium.

15. The bone screw of claim 12, wherein the magnet is constructed from neodymium.

16. A bone screw configured to be screwed into a bone, comprising:
    an exterior casing;
    a head having a recess on a top end, the recess being configured to receive a means for driving the bone screw into the bone;
    a tip having a distalmost point configured to be driven into the bone;
    a shaft extending between the head and the tip;
    a magnet having a north pole and a south pole;
    an interior cavity within the bone screw configured to house the magnet, the interior cavity being located inside of the head;
    wherein the exterior casing encloses the tip, the shaft, and the head, and wherein a portion of the exterior casing enclosing the shaft comprises a set of exterior threads; and
    wherein the magnet is encased within the bone screw with no portion of the magnet exposed outside of the exterior casing.

17. The bone screw of claim 16, wherein a floor of the interior cavity is oriented at an angle greater than 90 degrees with respect to the shaft.

18. The bone screw of claim 16, wherein a floor of the interior cavity is oriented such that a length of the magnet extending between the north pole and the south pole is perpendicular to the shaft.

19. The bone screw of claim 16, wherein the exterior casing is constructed from titanium.

20. The bone screw of claim 16, wherein the bone screw is configured to be drilled into the bone of a user and aligned with a magnetic field external to the user.

* * * * *